United States Patent
McCarty et al.

(10) Patent No.: US 10,677,706 B2
(45) Date of Patent: *Jun. 9, 2020

(54) PROCESSES AND SYSTEMS FOR CHARACTERIZING AND OPTIMIZING FRACTURING FLUIDS

(71) Applicant: Chevron U.S.A. Inc., San Ramon, CA (US)

(72) Inventors: Douglas K. McCarty, Houston, TX (US); Jon E. Burger, Houston, TX (US); Lin Li, Albany, CA (US); Guo-Qing Tang, Mountain View, CA (US); Marcus O. Wigand, Missouri City, TX (US); Varadarajan Dwarakanath, Houston, TX (US); Dyung Tien Vo, Houston, TX (US)

(73) Assignee: CHEVRON U.S.A. INC., San Ramon, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/229,616

(22) Filed: Dec. 21, 2018

(65) Prior Publication Data
US 2019/0128791 A1     May 2, 2019

Related U.S. Application Data

(63) Continuation of application No. 15/222,716, filed on Jul. 28, 2016, now Pat. No. 10,197,489.

(Continued)

(51) Int. Cl.
*G01N 15/08*     (2006.01)
*C09K 8/60*      (2006.01)
(Continued)

(52) U.S. Cl.
CPC .......... *G01N 15/082* (2013.01); *C09K 8/602* (2013.01); *C09K 8/605* (2013.01); *C09K 8/66* (2013.01); *C09K 8/68* (2013.01); *C09K 8/88* (2013.01); *E21B 43/26* (2013.01); *E21B 49/00* (2013.01); *E21B 49/08* (2013.01); *G01N 33/24* (2013.01); *C09K 2208/28* (2013.01)

(58) Field of Classification Search
CPC ...... G01N 15/082; G01N 33/24; C09K 8/602; C09K 8/605; C09K 8/66; C09K 8/68; C09K 8/88; C09K 2208/28; E21B 43/26; E21B 49/00; E21B 49/08
See application file for complete search history.

(56) References Cited

U.S. PATENT DOCUMENTS 10,197,489 B2     2/2019   McCarty et al.

OTHER PUBLICATIONS

Al-Bazali, T.M., et al.; "A Rapid, Rigsite-Deployable Electrochemical Test for Evaluating the Membrane Potential of Shales"; SPE 96098, (2005), pp. 1-14.

(Continued)

*Primary Examiner* — Sujoy K Kundu
*Assistant Examiner* — L. Anderson

(57) ABSTRACT

A workflow to optimize a fracturing fluid for injection into a subterranean formation is provided. The workflow comprises measurement of fundamental properties and characteristics of reservoir rock and fluid, their interaction with fracturing fluid, computer-based models and laboratory performance testing to select preferred fracturing base fluid and additives package for use in fracturing/re-fracturing stimulation of specific shale formations to enhance hydrocarbon recovery.

31 Claims, 6 Drawing Sheets

Related U.S. Application Data

(60) Provisional application No. 62/197,894, filed on Jul. 28, 2015.

(51) Int. Cl.

| | | |
|---|---|---|
| *E21B 49/00* | (2006.01) | |
| *E21B 49/08* | (2006.01) | |
| *E21B 43/26* | (2006.01) | |
| *C09K 8/66* | (2006.01) | |
| *C09K 8/68* | (2006.01) | |
| *C09K 8/88* | (2006.01) | |
| *G01N 33/24* | (2006.01) | |

(56) References Cited

OTHER PUBLICATIONS

Basu, Subhayu, et al.; "Measurement of Critical Disjoining Pressure for Dewetting of Solid Surfaces"; Journal of Colloid and Interface Science, vol. 181, (1996), pp. 443-455.

Chenevert, M.E., et al.; "Shale/Mud Inhibition Defined with Rig-Site Methods"; SPE Drilling Engineering, Sep. 1989, pp. 261-268.

Kuila, Utpalendu, et al.; "Nano-Scale Texture and Porosity of Organic Matter and Clay Minerals in Organic-Rich Mudrocks"; Fuel, vol. 135, (2014), pp. 359-373.

Kuila, Utpalendu, et al.; "Specific Surface Area and Pore-Size Distribution in Clays and Shales"; Geophysical Prospecting, (2013), vol. 61, pp. 341-362.

McCarthy, Kevin, et al.; "Basic Petroluem Geochemistry for Source Rock Evaluation"; Oilfield Review, Summer 2011, vol. 23, No. 2, pp. 32-43.

PROCESSES AND SYSTEMS FOR CHARACTERIZING AND OPTIMIZING FRACTURING FLUIDS

CROSS-REFERENCE TO RELATED APPLICATIONS

The present application claims priority and benefit as a continuation patent application from U.S. application Ser. No. 15/222,716, filed on Jul. 28, 2016, which is incorporated by reference in its entirety. This application claims benefit under 35 USC 119 of U.S. Provisional Patent App. No. 62/197894 with a filing date of Jul. 28, 2015, which is incorporated herein by reference in its entirety and for all purposes.

TECHNICAL FIELD

The invention relates generally to systems and methods for characterizing and optimizing fluids for use in fracturing a subterranean formation to improve production and hydrocarbon recovery.

BACKGROUND

Unconventional development of oil and gas shale and tight reservoirs has globally become very active in the past ten years due to advances in hydraulic fracturing operations. Due to the tightness of the shale rock formations (generally much less than 1-md and often measured in nano-darcy), hydraulic fracturing enables enhanced production by providing more contacts with the reservoir and allow ease of fluid production into the wellbore.

Hydraulic fracturing generally entails injecting a fluid into the wellbore at a sufficient rate and pressure to part or open existing fractures and/or overcome the tensile strength of the formation and, in the case of shallow, horizontal fractures, the formation overburden pressure. The injected fluid ("fracturing fluid") creates cracks or fractures extending from the wellbore out into the formation, which may be often propped open with a proppant entrained in the fluid. The fractures permit hydrocarbons and other fluids to flow more freely into or out of the wellbore.

It is desirable to optimize the physical and chemical properties of a fracturing fluid. A fracturing fluid should be compatible with the reservoir rock and reservoir fluids, have sufficient viscosity and structure to suspend proppants if present, and transport them deep into the formation, be stable enough so as to retain sufficient viscosity and structure throughout proppant placement, possess low fluid losses properties, be easily removed from the formation, present low fluid flow friction pressures, be easily made under field conditions, be relatively inexpensive, and exhibit high levels of rheological performance.

Each shale play and reservoir inherently contains different rock and fluid types of varying properties. The reservoir interaction to a specific fracturing fluid can vary significantly and result in different production outcomes. In the prior art, different fracturing fluid compositions are tested for a particular reservoir until one chemistry (composition) is found that provides fracture effectiveness for operation and cost. The trial-and-error process can consume significant time and cost until a fluid is found for a particular reservoir.

Different types of fracturing fluids have been tried in the prior art. Dispersing fracture fluids are those which include aqueous solutions of monovalent cation salts, including organic sulfates, phosphates, chlorides, fluorides, citrates, acetates, tartrates, hydrogen phosphates or a mixture thereof. A dispersing fracture solution in the fracture zone will disperse clays and other earthen particles and allow them to be carried by the flow-back fluids out of the hydrocarbon producing fracture zone. This process increases hydrocarbon production when the pay zone does not contain a lot of clay. Aggregating fracture fluids are those which include aqueous solutions of di- and trivalent cation salts, e.g., calcium chloride ($CaCl_2$), iron chloride ($FeCl_3$), magnesium chloride ($MgCl_2$), di- and trivalent metal salts of carboxylic acids. An aggregating fracture solution will aggregate and bind clays and other earthen materials. This stabilizes the fracture zone but will eventually clog and occlude the pay zone with the clay particles that are not aggregated by the cation salts. Many fracturing fluid materials when used in un-optimized concentrations have relatively poor "clean-up" properties, meaning that such fluids undesirably reduce the permeability of the formation and proppant pack after fracturing the formation.

There is still a need for improved methods and systems to characterize and optimize fracturing fluid chemistry. There is also a need for improved methods and systems to optimize fracturing fluid chemistry taking into consideration of factors including but not limited to imbibition, diffusion and interrelations between the fracturing fluid and reservoir rock in the fracturing fluid chemistry optimization (FFCO).

SUMMARY OF THE INVENTION

Embodiments of optimizing fracturing fluids are provided herein. One embodiment of a method for optimizing fracturing fluid compositions for injection into a subterranean formation includes providing a plurality of rock samples being representative of a rock matrix within a subterranean formation containing hydrocarbons for recovery; providing a plurality of brine samples being representative of formation brines of the subterranean formation; providing a plurality of hydrocarbon samples being representative of hydrocarbons recoverable from the subterranean formation; characterizing the rock samples to obtain one or more rock parameters representing geochemistry properties of the rock samples, petrophysical properties of the rock samples, or any combination thereof; characterizing the brine samples to obtain one or more brine parameters representing alkalinity properties of the brine samples, salinity properties of the brine samples, total dissolved solids (TDS) properties of the brine samples, or any combination thereof; characterizing the hydrocarbon samples to obtain one or more hydrocarbon parameters representing acidity properties of the hydrocarbon samples, polarity properties of the hydrocarbon samples, molecular characteristics properties of the hydrocarbon samples, or any combination thereof; synthesizing at least two fracturing fluid samples based on the rock parameters, the brine parameters, the hydrocarbon parameters, or any combination thereof; and conducting a test on at least one rock sample and the at least two fracturing fluid samples to evaluate rock-fluid interactions. The test comprises an interfacial tension test to determine contact angle, zeta potential, wettability, interfacial tension properties, or any combination thereof; an ion selectivity test to determine ion selectivity properties; a cation exchange capacity test to determine cation exchange capacity properties; a disjoining pressure test to determine disjoining pressure properties; an adsorption desorption simulation test to determine cation exchange and charge compensation properties; a forced imbibition test to evaluate kinetic and mass transfer properties; or any combination thereof. The method further includes preparing at least one fracturing fluid for injection into the subterranean formation based on at least two criteria, wherein the criteria comprises the rock parameters, the brine parameters, the hydrocarbon parameters, the contact angle properties, the zeta potential properties, the wettability properties, the interfacial tension properties, the ion selectivity properties, the cation exchange capacity properties, the disjoining pressure properties, the cation exchange and charge compensation properties, the kinetic and mass transfer properties, or any combination thereof.

DETAILED DESCRIPTION

Figure 1:
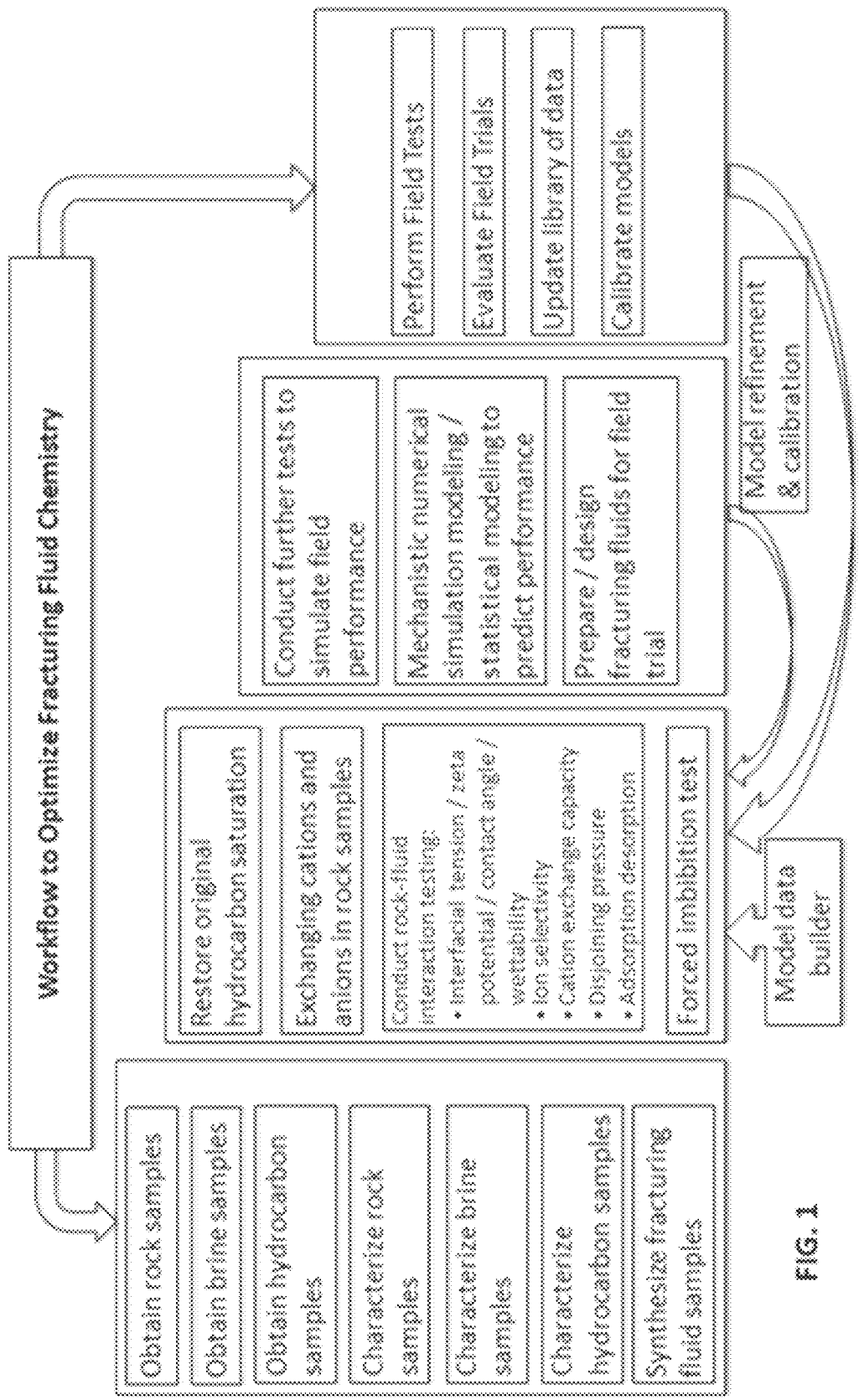
FIG. 1 illustrates a schematic diagram showing the steps carried out in a method for developing at least one optimized fracturing fluid for a hydraulic fracturing operation, according to one embodiment.

The following terms will be used throughout the specification and will have the following meanings unless otherwise indicated.

"Hydrocarbons" or "hydrocarbonaceous" or "petroleum" or "crudes" may be used interchangeably to refer to carbonaceous material originating from subterranean sources as well as synthetic hydrocarbon products, including organic liquids or gases, kerogen, bitumen, crude oil, natural gas or from biological processes, that is principally hydrogen and carbon, with significantly smaller amounts (if any) of heteroatoms such as nitrogen, oxygen and sulfur, and, in some cases, also containing small amounts of metals. Crude oil (e.g., liquid petroleum) and natural gas (e.g., gaseous petroleum) are both hydrocarbons.

"Hydraulic fractures" are fractures or cracks which are introduced into a subterranean formation by injecting a fluid into the formation at a pressure greater than the parting or fracture pressure of the formation. Hydraulic fractures can have a substantially vertical orientation at depths greater than about 350 meters, and the parting or fracture pressure is the pressure at which open fractures are created, either by opening existing closed fractures or exceeding the rock tensile stress. Fractures can also be substantially horizontal, and the parting pressure may be the overburden pressure or the sum of the overburden pressure and the tensile stress of the formation.

"Well" and "wellbore" are used interchangeably to denote a borehole extending from the earth surface to a subterranean formation and at least partially in fluid communication with a subterranean formation.

A "production wellbore" enables the removal of fluids from the formation to the surface and an "injection wellbore" enables the placement of fluid into the formation from the surface. In hydraulic fracturing, the production wellbore may temporarily have an injection function or used as an injection wellbore for placement of the fracturing fluid in the formation.

"Fluid" is inclusive of a gas, a liquid, and/or mixtures thereof.

"Fracturing fluid" or "frac fluid" refers to the fluid that is pumped into the well to create conductive fractures. The fracturing fluid can be any of water-based fluids, viscosified water-based fluids, non-viscosified water-based fluids, gelled oil-based fluids, acid-based fluids, foam fluids, and mixtures thereof.

"Formation brine" or "formation water" refers to water that occurs naturally within the pores of the inorganic matrix of the subterranean formation. "Connate brine" or "connate water" refers to water that is trapped in the pores of a rock during its formation.

"Imbibition" refers to a process of absorbing a wetting phase, e.g., a fluid, into a rock and in one embodiment, displacing another fluid in the process. "Spontaneous imbibition" refers to the process of absorption with no pressure driving the phase into the rock. It is possible for the same rock to imbibe both water and oil, with water imbibing and displacing excess oil from the surface of the rock grains. It is also possible for oil to imbibe, displacing excess water from the surface of the rock grains.

"Wettability" refers to the preference of a solid, e.g., a rock, to contact one liquid or gas, e.g., a fluid or a wetting phase, rather another fluid. The wetting phase will tend to spread on the solid surface and the solid will tend to imbibe the wetting phase and displace a non-wetting phase. There is a correlation between the wettability property of a rock and its properties such as relative permeability, electrical properties, nuclear magnetic resonance relaxation time, and saturation profiles in the reservoir. A rock can be water wet, oil wet, or intermediate wet. In one embodiment, wettability is indicated or measured by using the Amott test, which combines two spontaneous imbibition measurements and two forced displacement measurements, defining two different indices: the Amott water index $I_w$ and the Amott oil index $I_o$. The indices are combined to give the Amott-Harvey index ($AI=I_w-I_o$), which results in a number between +1 (strongly water-wetting) and −1 (strongly oil-wetting).

"Intermediate wet" refers to a state that can be mixed-wet, in which some surfaces or grains are water wet and some are oil-wet, or a neutral-wet, in which the surfaces or grains are not strongly wet by either oil or water.

"Zeta potential" is a parameter characterizing electrochemical equilibrium on interfaces, wherein the zeta potential depends on the properties of liquid as well as on properties of the surface. Zeta potential may be calculated from electrophoretic mobility measurements in which an electrical current is passed via electrodes through an aqueous suspension consisting essentially of formation mineral colloidal particles, and determining the direction and speed of the colloidal movement.

"Salt" refers to a composition of at least one cation and at least one anion that forms ions in aqueous solution. The ions may include such cations as sodium, potassium, calcium, barium, magnesium, ammonium, tetraalkylammonium, and the like. The salts may also include such anions as chloride, bromide, iodide, carbonate, bicarbonate, sulfate, bisulfate, borate, phosphate, nitrate, silicate, acetate and citrate, and the like. Compositions containing salts may be referred to as "salinities."

"Interfacial tension" or "IFT" refer to the surface tension between various rock-fluid interfaces (e.g., oil and water) due to different salinities and different concentrations.

"Cloud point" refers to a temperature point at which a compound becomes insoluble in an aqueous solution, the temperature at which the compound becomes hydrophobic enough to separate from the aqueous solution, becoming a colloidal suspension or macro-emulsion.

"Water-sensitive minerals" refers to minerals that when contacted by aqueous fluids in disequilibrium with the minerals in the formation, the minerals tend to swell and/or migrate.

In hydraulic fracturing, hydrocarbon is recovered from a formation where rock is fractured by a pressurized liquid. Hydraulic fracturing involves the high pressure injection of a fracturing (fracking) fluid into a wellbore. The fracturing fluid is primarily water with sand and/or other proppants, injected into the wellbore to create cracks through which hydrocarbons (e.g., gas and/or crudes) and formation brines can flow. When the hydraulic pressure is ceased to apply to the well, the proppants hold the fractures open for the recovery of hydrocarbons (and formation brine) from the same wellbore.

Contact between any fracturing fluid with the surface of minerals is accompanied by adsorption. There are two types of adsorption: physical and chemical. One distinction between physical and chemical adsorption is in the differences of the forces that hold adsorbed molecules on a solid surface. Forces of electrostatic origin such as the Van deer Waals forces are responsible for the physical adsorption. If acting forces are of chemical nature (e.g., exchanges forces), then such adsorption is called chemical.

It is believed that with the selection/design of the right chemistry for the fracturing fluid composition, fracture effectiveness as well as long-term well performance can be enhanced. This invention relates to improved methods and systems, overcoming the trial-and-error approach of the prior art, to optimize the design and selection of fracturing fluid for use in hydraulic fracturing. The systemic approach includes comprehensive data collection and analysis to capture the key influencing physics and predictive methods, both statistical and mechanistic modeling, to enable the selection of optimal fracturing fluids designed for tight rock formations or shale plays.

In one embodiment, the method relates to systematic assessment of rock-fluid interactions to evaluate, design, and select fracturing fluid(s) applicable to specific rocks or reservoirs. The systematic assessment is suitably for any type of rock formation, including tight gas, oil, shale, carbonate, coal reservoirs, e.g., including shale rock with very low permeability much less than 1-md such as 0.00001 md, and measured in nano-darcy. The systematic assessment takes into account the physical and chemical adsorption characteristics of the fracturing fluid, i.e., brine water and organic compounds and molecules on rock and mineral surfaces and within their aggregate pore systems, including molecular interactions via charge compensation and other mechanisms between the hydrocarbon molecules and mineral and organic surfaces at the atomic level. The assessment also takes into account imbibition as one of the determining parameters, specifically spontaneous imbibition, which is the imbibition by action of capillary pressure when a core sample is surrounded by a fracturing fluid/brine. FIG. 1 is a schematic diagram showing the steps carried out in a systematic method for developing a fracturing fluid for a hydraulic fracturing operation, according to one embodiment.

Figure 2:
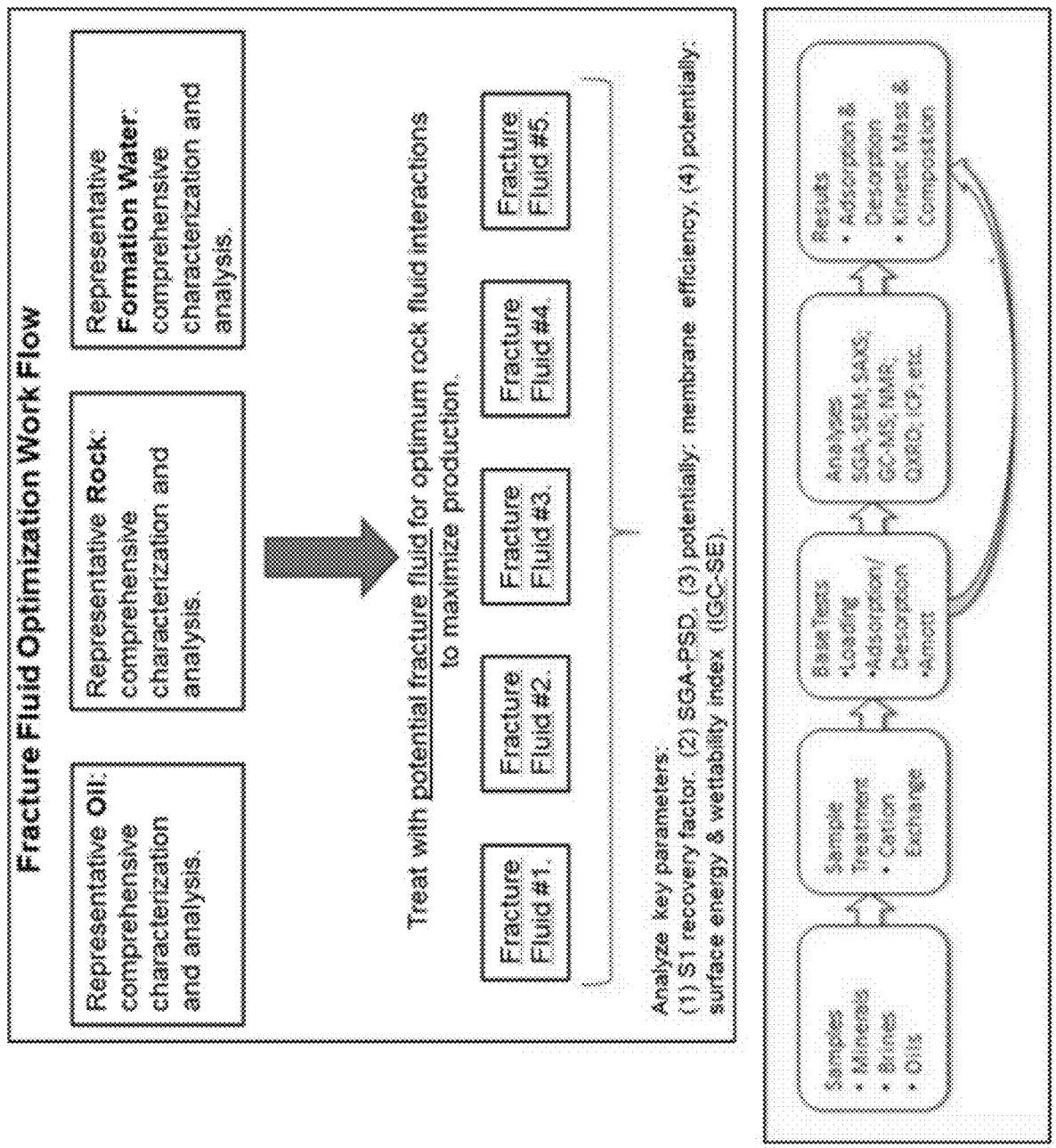
FIGS. 2A-2B illustrate schematic diagrams showing various samples and tests that can be utilized in a method for tailoring a fracturing fluid for a particular reservoir/rock formation, according to one embodiment.

In order to optimize fracture fluids for maximum production, it is necessary to have an objective understanding and comparison between candidates related to the rock properties controlling fluid transport and phase wettability. Following fundamental characterization of the oil, rock and formation water in a field of interest, aliquot samples will be treated with potential fluid compositions not limited to a specific number (FIGS. 2A-2B). For each rock test candidate, characterization includes a number of key tests or measurements to represent the rock characteristics.

Rock Samples: One of the steps in the method is obtaining a library of rock samples in different forms and from different reservoirs, including but not limited to samples of mineral standards and core plugs. The rock samples can be shale materials, e.g., laminar shales, dolomitic shales, limy shales, etc., and combinations thereof. Mineral standards may include sandstone, clay, non-clay minerals, quartz and calcite. The rock samples can be obtained from wellbores, e.g., core samples from exploratory wells, production wells, wells being drilled or have been drilled. The rock samples can also be from cuttings present in the returns of a well being drilled. The rock samples can be "artificial" core samples, e.g., mixture of rocks from various locations. The rock samples can be any of powdered form, individual or composite samples from rock formations, discs, core plugs, crushed materials, suitable for tests to obtain representative characteristics of the reservoirs.

In one embodiment, the library includes at least one mineral that has a negative zeta potential (i.e., a negative surface electric charge) under reservoir condition. In another embodiment, the library includes a variety of minerals from various rock formations, e.g., smectite low charge, smectite high charge, illite, quartz, calcite, mixed-layered illite-smectite, and kaolinite. In yet another embodiment, the library includes samples of water-sensitive mineral or several species, e.g., silica; iron minerals; alkaline earth metal carbonates, feldspars, biotite, illite, and chlorite; smectite clays such as montmorillonite, beidellite, nontronite, saponite hectorite and sauconite; kaolin clays such as kaolinite, nacrite, dickite, endellite and halloysite; illite clays such as hydrobiotite, glauconite and illite; chlorite clays such as chlorite, greenalite and chamosite; other clay minerals not belonging to the above groups such as vermiculite, palygorskite, sepiolite; mixed-layer (both regular and irregular) varieties of the above minerals; and any combination thereof.

In one embodiment, the library includes a number of artificial core samples, e.g., mixtures of quartz, silica, etc., compacted in a specific demountable forms and burnt gradually at different temperatures, e.g., 300° C., 500° C., 800° C., etc., simulating rock samples in certain formations/reservoirs.

Hydrocarbon Samples for Rock-Fluid Interaction Assessment: In one embodiment, samples of crudes from reservoirs in the library are also assembled for the systematic assessment. The crudes of different characteristics can provide an array of interactions with the fracturing fluids based on their polarity (e.g., polar and non-polar), acidity (e.g., highly acidic, highly basic), and differences in molecular content. In one embodiment, the collection includes crudes with significant polar organic molecules and high asphaltene (C10+) contents, crudes with a non-polar characteristic and relatively high asphaltene, and crudes as well as condensate with a higher proportion of lighter molecules (<C10).

In one embodiment, the hydrocarbon samples also include model and/or synthetic compounds, e.g., decane, mineral oil. In another embodiment, model hydrocarbon compounds representative of certain crude oil classes, e.g., aliphatic, aromatic, resins, asphaltenes, etc., are provided for testing to monitor adsorption/desorption processes as a result of cation exchange processes and related changes in wettability.

Brine: In one embodiment, brine or water samples produced from the same or nearby formations of the reservoirs (for the rock samples) may be gathered for analyses, particularly when the brine may be used as the water source for the fracturing fluid. Such formation water may contain amounts (concentration) of precursor ions, such as divalent sulfate ($SO^{4-}$) which may form insoluble salts when they come into contact with cations, such as $Ba^{++}$, $Sr^{++}$, and $Ca^{++}$ resident in the formation. The water may be injected into the formation by itself (unprocessed as produced water) as a component of the fracturing fluid, or it can be treated using a strainer, and/or multimedia filters, and/or a membrane based system.

Water for Fracturing Fluid: Water for use in "designing" the fracturing fluids may be from any source, provided that it does not contain components that might adversely affect the stability and/or performance of the first treatment fluids or second treatment fluids of the present invention. The water can be from a fresh water source, or include brines (formation and/or synthetic brines). Examples of suitable brines may include, but are not necessarily limited to, heavy brines, monovalent brines, divalent brines, and trivalent brines that comprise soluble salts like sodium chloride, calcium chloride, calcium bromide, zinc bromide, potassium carbonate, sodium formate, potassium formate, cesium formate, sodium acetate, potassium acetate, calcium acetate, ammonium acetate, ammonium chloride, ammonium bromide, sodium nitrate, potassium nitrate, ammonium nitrate, ammonium sulfate, calcium nitrate, sodium carbonate, potassium carbonate, any combination thereof, and any derivative thereof.

In one embodiment, the fracturing fluid is a mix of fresh water and brine with optional addition of monovalent/multivalent cations. A plurality of synthetic brine samples may be provided for the systematic assessment, e.g., brine samples at different concentrations of 0.02, 0.25, 0.50, 1, 2 and 5N (N, normality in volume per liter) with various salts including but not limited to NaCl, KCl, $CaCl_2$, $MgCl_2$, $AlCl_2$, $NH_4Cl$ and mixtures thereof.

In one embodiment with the use of formation brine, the formation brine may be first treated with the removal of some monovalent and/or multivalent cations, e.g., removal of about 60-90% of the cations present, along with the associated anions such as chloride, fluoride, and bromide. In another embodiment, after the removal of some of cations, some other cations can be added (e.g., monovalent and/or multivalent cations) to the brine water.

Additives For Use in Fracturing Fluid: In one embodiment instead of or in addition to the various salts to make up a fracturing fluid, various additive chemicals are added for the fracture treatment. In one embodiment, low concentrations (<2 wt. %) of between 3 and 12 additive chemicals are added to each fracturing fluid sample. The selection and amount added depends on the characteristics of the water and the formation being fractured. Examples may include but are not limited to fluid loss control additives, nucleophilic agents, biocides, friction reducers, pH reducing agents, soaps (surfactants), polymers and mixtures thereof.

In one embodiment, some of the fracturing fluids include amounts of non-ionic chemical to help release the oil trapped in the pore spaces. In another embodiment, some of the fracturing fluids include surfactants to help reduce the interface tension (IFT) between the water and the oil allowing the trapped oil to escape from the pore spaces. The surfactants can also help alter the wettability of the reservoir rock and help reduce the adsorption of the non-ionic chemicals by the reservoir rock. Examples of non-ionic chemicals include compounds that are soluble in the fracturing fluid, e.g., having HLB (hydrophilic lipophilic balance) greater than 10, and cloud point (CP) above surface and reservoir temperature (e.g., between 30 to 150° C.).

In one embodiment, the fracturing fluids for the study include 0.05 to 5 vol. % of non-ionic chemicals or surfactants selected from alcohol alkoxylates, alkyl alkoxylated esters and alkyl polyglycosides. In another embodiment, at least some of the fracturing fluids further comprise amounts of hydrophobically-modified cationic polymers. In another embodiment, the fracturing fluids include amounts of aqueous-miscible fluids, e.g., alcohols, glycerin, glycols, polyglycol amines, polyols, any derivative thereof, or any combination thereof. Examples of suitable alcohols may include, but are not necessarily limited to, methanol, ethanol, propanol, iso-propanol, butanol, tert-butanol, and the like. Examples of suitable glycols may include, but are not necessarily limited to, polyglycols, propylene glycol, ethylene glycol, and the like.

In some embodiments, the fracturing fluid samples may further include a gas, and/or a foaming agent. Suitable gases for use in the fracturing fluid may include, but are not limited to, nitrogen, carbon dioxide, air, methane, helium, argon, and any combination thereof. Suitable foaming agents include cationic foaming agents, anionic foaming agents, amphoteric foaming agents, nonionic foaming agents, or any combination thereof.

Compatability: The fracturing fluid evaluation and optimization process may include fracture fluid compatibility tests to ensure fracture fluid may not negatively impact the formation rock (mineralogy) and/or formation fluids. Compatability tests include, but are not limited to, fracturing fluid and fluid additive compatibility test of planned source water and planned fracturing fluid system, fracturing fluid and proppant compatibility test, fracturing fluid and formation fluid compatibility, or any combination thereof. Signs of incompatibility through these tests include clouds, precipitates, phase separation, etc. If any incompatability is determined, the incompatability may be addressed and/or compatible alternatives may be pursued.

As an example, one embodiment includes verifying compatibility of components in the at least one fracturing fluid before injection into the subterranean formation. As another example, one embodiment includes verifying compatibility of the at least one fracturing fluid with at least one other fluid that will also be injected into the subterraenan formation before injection of the at least one fracturing fluid into the subterranean formation.

The surfactant in a fracturing fluid to be injected may also be checked for compatibility. For example, in one embodiment, where the at least one fracturing fluid for injection into the subterranean formation includes a surfactant, the embodiment includes verifying the compatibility of the surfactant with at least one other additive of the at least one fracturing fluid before injection of the at least one fracturing fluid into the subterranean formation. As another example, in one embodiment, where the at least one fracturing fluid for injection into the subterranean formation includes a surfactant, the embodiment includes verifying the compatibility of the surfactant with a temperature condition of the subterranean formation, a salinity of a formation brine of the subterranean formation, hydrocarbons in the subterranean formation, or any combination thereof before injection of the at least one fracturing fluid into the subterranean formation. For example, brine samples and hydrocarbon samples that were previously obtained may be used for this verification. Alternatively, new brine samples, new hydrocarbon samples, or both may be obtained for this verification. The temperature condition may be obtained using at least one temperature sensor.

Library (Database) with Data Characterizing Rock-Fluid Interactions & Effects: In the following sections, the term brine may be used interchangeably with "fracturing fluid" or "fluid," in reference to the fluid samples being tested to provide data for the library, whether it's formation brine, synthetic brine, or a "designed" fracturing fluid for testing with the rock samples from the reservoirs collected for the systematic assessment.

In one embodiment, a wide variety of tests are carried out with the rocks and fluid samples to characterize rock-fluid interactions and their combined effects on the recovery of hydrocarbons, e.g., potential wettability changes due to imbibition process, mass transfer kinetics of diffusion, etc. Due to the tight nature of shale formations with extremely low porosity and permeability, molecular interactions occur very slowly, with measurements over time being collected for the library of test results.

The library can grow overtime with additional molecular interaction measurements and data for new reservoirs under evaluation. The library contains measurements related to molecular material exchanges (e.g., adsorption/desorption) and hydrocarbon release (e.g., kinetic imbibition) from rock-fluid interactions, with experiments with minerals, formation rocks, brines and additives (as fracturing fluids), and crude oils of various compositions and sources, simulating different formation conditions (e.g., pressure, temperature). The library can also include data from actual field trials with existing reservoirs and implemented fracturing fluids. Data from the library facilitates future focus experiments for specific interactions of relevant organic molecules, hydrocarbon fluids, and rock types with fracturing fluids for a new reservoir under study. FIG. 1 is a schematic diagram illustrating various samples and tests that can be utilized in building a library for use to optimize a fracturing fluid for a particular reservoir/rock formation, according to one embodiment.

Preparation of Rock Samples: In some embodiments, reservoir rock samples are collected from preserved core or core that still contains significant crude oil saturation. In some embodiments, before the experiments are conducted to evaluate the interactions of the fracturing fluid for particular reservoirs, e.g., wettability measurements, the rock samples are "restored" to mimic the reservoir conditions. In some embodiments, the plugs from the targeted reservoirs are saturated with fluids, e.g., formation water, hydrocarbons from the formation, or model hydrocarbons prior to characterization, measurements, or experiments.

In one embodiment to ensure the complete saturation of the samples, the selected cores are placed in a pressure chamber with multiple access ports with at least one port being connected to a vacuum source, while at least another port is connected to the saturation fluid source. This air tight pressure vessel is put under vacuum for a few hours to ensure that all air is removed from the vessel. After air evacuation, a prepared saturation fluid is allowed to fill the pressure vessel. Once the pressure vessel is filled with the saturation fluid, the liquid pressure is increased slowly, e.g., to 1000 psig, and allowed to stabilize under pressure for 4 hours. At the end of this stabilization time, the pressure in the chamber can be reduced and de-pressurized. The samples can be removed and saturated with a fluid, e.g., hydrocarbons, brine, etc.

Characterizing Petrophysical/Geochemistry Properties: The rock samples collected are tested to gather geochemistry information and conduct petrophysical analyses including but not limited to permeability, surface area, pore volume, porosity, and/or matrix density. The rock samples can be characterized/analyzed both before and after certain experiments, e.g., imbibition or cation exchange experiments.

Methods to characterize rock samples to obtain mineral composition, mineral structure, permeability, pore volume, pore structure, and fluid compatibility include but are not limited to QXRD (quantitative X-ray diffraction), Fourier transform infrared spectroscopy (FTIR), CEC (cation exchange capacity), detailed clay analysis, TOC (total organic carbon), Rock-Eval™ pyrolysis, SCA (special core analysis), pyrolysis gas chromatography (py-GC/MS), Poro-Perm™ method, Mercury Injection Capillary Pressure (MICP), water immersion porosimetry, relative permeability, Klinkenberg permeability, NMR (nuclear magnetic resonance to measure fluid saturation), thermal gravimetric mass spectrometry (TGMS), and/or microscopy (e.g. light microscopy and scanning electron microscopy). In one embodiment, QXRD and FTIR are used to reveal the structural and crystal chemical variety in the rock samples, e.g., composition ranges and identification criteria for mica varieties in the rock samples.

Methods for geochemistry evaluation/characterizing rocks are described in: "Specific surface area and pore-size distribution in clays and shales" by Kuila et al., Geophysical Prospecting, 2013, 61, 341-362; "Basic Petroleum Geochemistry for Source Rock Evaluation" by McCathy et al., Oilfield Review Summer 2011:23, no. 2; "Nano-scale Texture and Porosity of Organic Matter and Clay Minerals in Organic-Rich Mudrocks" by Kuila et al., Fuel 135 (2014) 359-373; each of the references are incorporated herein by reference.

In one embodiment, the permeability measurements are carried out on the samples with a gas permeameter applying Klinkenberg effect corrections to obtain the liquid permeability. In another embodiment, the rock samples undergo micro-CT/nano-CT imaging to provide formation fracture characteristics. In one embodiment, porosity measurements are carried out using any of helium porosimetry-mercury immersion (HPMI), mercury injection capillary pressure (MICP) and nuclear magnetic resonance (NMR).

Figure 3:
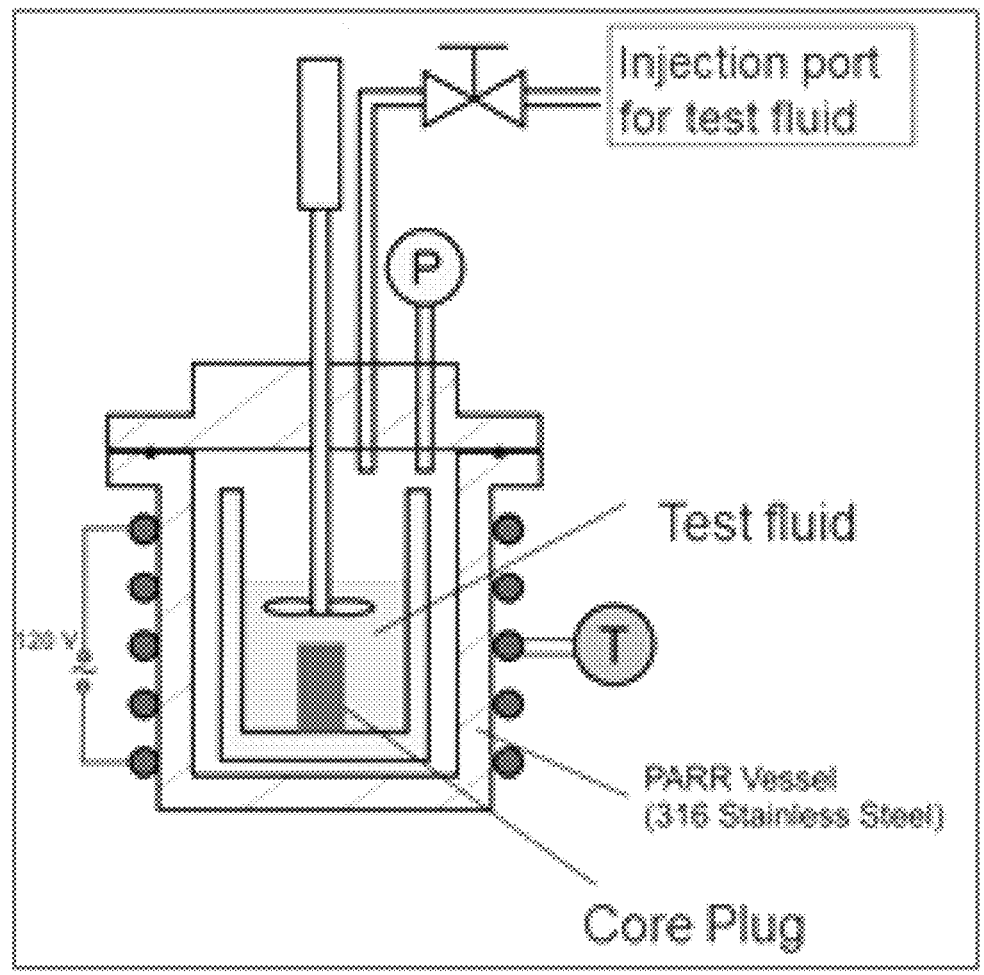
FIG. 3 illustrates a schematic diagram of a reaction vessel for an enhanced imbibition test, according to one embodiment.
Figure 4:
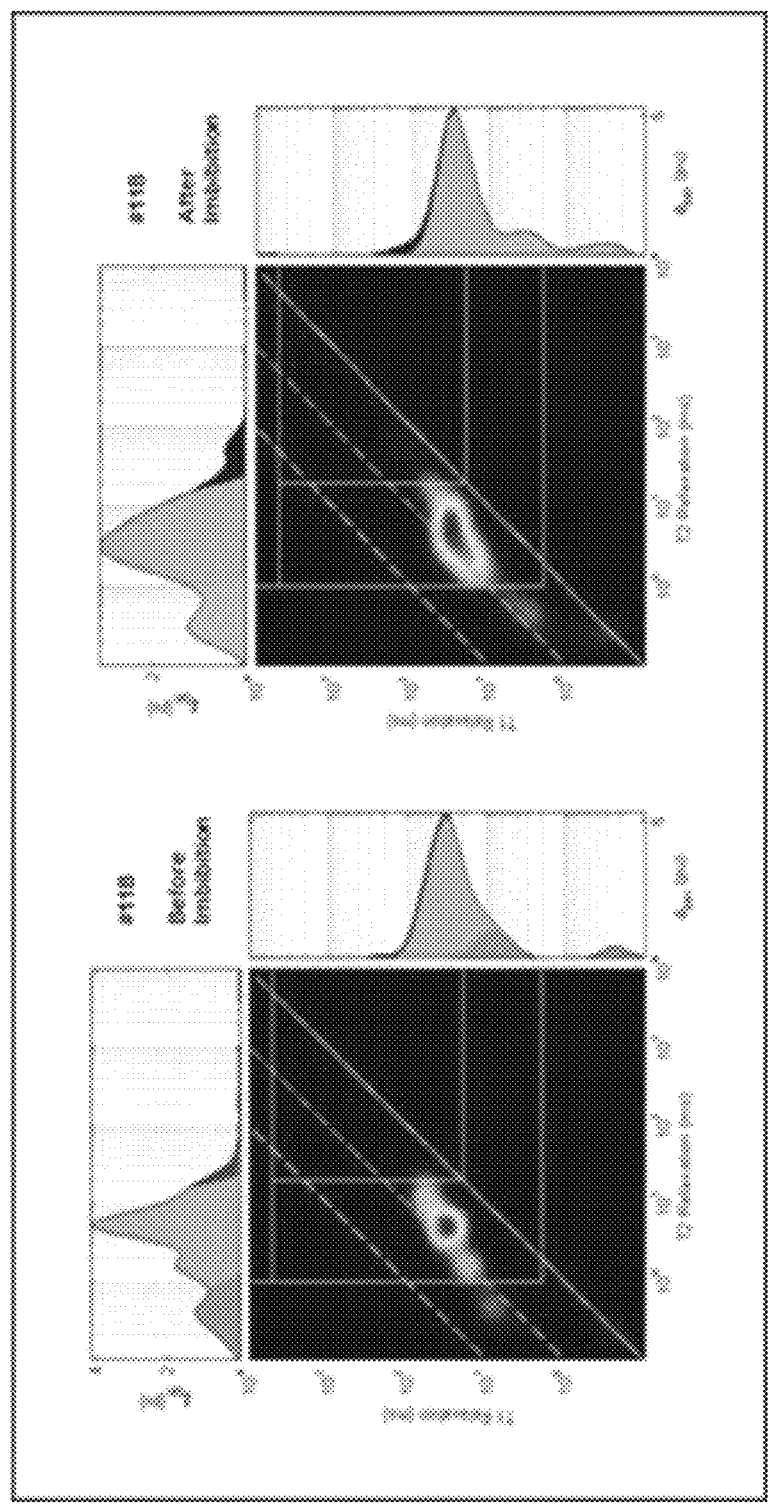
FIG. 4 illustrates NMR T1-T2 measurements before and after treatment, according to one embodiment.

The measured rock properties are used in potential fracture fluid design. In some embodiments, fracture fluid effects are evaluated by methods described previously along with two significant methods. The first is that potential fracture fluids are tested on liquid hydrocarbon saturated core plug samples in a hydrothermal reaction vessel at moderate temperature and pressure for various lengths of time (FIG. 3). Core plugs will initially undergo standard 2D T1-T2 NMR analysis before and after treatment (FIG. 4). A detailed experimental procedure is described in the below:

---

Plug and fluid characterization prior to NMR analysis
    Obtain standard end-trims and process for: WIP-RockSat porosity,
    oil and water saturation. Obtain SGA-$N_2$ isotherm and PSD.
    Obtain NMR spectra on pure saturation fluids
NMR Plug Procedure
Receive shale plugs at as-received condition:
    Record the weight for each plug;
    NMR measurement (T1-T2 and/or D-T2) to determine the initial -continued saturation of each plug;
Vacuum dry the shale plugs at 80° C. (Temperature and time used for drying are tentative). Upon completion of vacuum drying:
    Record the weight for each plug;
    NMR measurement (T1-T2 and/or D-T2) to determine the saturation of remaining fluid;
Saturate the shale plugs with decane. Vacuum will be pulled on the samples to around 0.3 Torr before pressurizing the decane to 2000 psig. The decane saturation for shale plugs usually last 4 to 5 days and the pressure is kept at 2000 psig. Upon completion of decane saturation:
    Record the weight for each plug;
    NMR measurement (T1-T2 and/or D-T2) to determine the porosity at 100% decane saturated condition;
    Calibrate the NMR porosity with core porosity;
Submerge the decane saturated shale plugs in designated solution with moderate pressure. The time used for the imbibition and reaction varies. Upon completion:
    Record the weight for each plug;
    NMR measurement (T1-T2 and/or D-T2) to determine the oil saturation and the solution saturation after surfactant treatment;
    Calculate the oil recovery factor;
    Estimate the penetration of solution into the pore space during the imbibition;
Evacuate the post-treatment shale plugs to remove movable oil. If this step is applicable, upon completion:
    Record the weight for each plug;
    NMR measurement (T1-T2 and/or D-T2) to determine the residual oil saturation;
    Calculate oil recovery factor based on NMR results;
    Calibrate with oil recovery factor based on mass balance;
Vacuum dry the shale plugs at 80° C. (Temperature and time used for drying are tentative). Upon completion:
    Record the weight for each plug;
    NMR measurement (T1-T2 and/or D-T2) to determine the saturation of remaining fluid;
Re-saturate the shale plugs with brine. Same procedure as shown in Step 3. Upon completion:
    Record the weight for each plug;
    NMR measurement (T1-T2 and/or D-T2) to determine the porosity at 100% brine saturated condition;
    Calibrate the NMR porosity with core porosity.

In addition to the above procedures and protocols, surface energy related to oil/water wettability and other properties will be conducted with the technique referred to as inverse gas chromatography surface energy analysis (IGC-SE). Inverse gas chromatography is a physical characterization technique that is used in the analysis of the surfaces of solids. IGC is a sensitive and versatile gas phase technique used to study the surface and bulk properties of materials in powder or granular form, where the roles of the stationary (solid) and mobile (gas or vapor) phases are inverted. In IGC, a single gas or vapor (probe molecule) is injected into a column packed with the solid sample under investigation. Instead of being a separation and analysis technique, as in normal gas chromatography (GC), IGC is considered a materials characterization technique.

Characterizing Injection Fluid (Brine) Properties: Samples of injection fluid, e.g., formation brine, recycled water, sea water, etc. are analyzed for properties including alkalinity, salinity, total dissolved solids (TDS) properties, e.g., amounts and types of cations and associated anions.

Characterizing Hydrocarbons Properties: Samples from the various formations are analyzed for properties and characteristics, e.g., resins, aromatics, carboxylic acids, etc., including but not limited to polar organic molecules and asphaltene (C10+) contents.

Obtaining Contact Angle/Zeta Potential/Interfacial Tension Measurements: One factor in the determination of the wettability of crude oil/mineral systems is the electrical or zeta potential of the crude oil/brine interface and the mineral/brine interface. Mineral here refers to the formation rock. Brine here refers to the fracturing fluid under consideration. Any of contact angle/zeta potential/interfacial tension data measurements can be obtained using methods known in the art. Contact angle and zeta potential can be measured using electrochemical sensing technology and commercially available instruments. Interfacial tensions can be measured using a spinning drop tensiometer or calculated from phase behavior experiments. Wettability measurements can be carried out before and after certain experiments, e.g., imbibition or cation exchange experiments.

Data is collected correlating the changes in zeta potential, contact angle, interfacial tension from various rock samples as a function of variables including but not limited to temperature, pH/salinity, and compositions of the fracturing fluid samples. In one embodiment, the measurements are conducted with a Kruss DSA 100 apparatus equipped with software to capture contact angle and IFT data. The range and accuracy of the contact angle measurement are from 0° to 180° with a resolution of +/−0.1. The IFT measurements range from 0.01 to 100 mN/m with a resolution of 0.01 mN/m. Digital imaging can also be provided from this equipment.

In the tests, sample drops of the brine and/or fracturing fluid are injected onto the test surface of the rock samples. Once the droplet became stable, the parameters of the fluids, drop phase and surrounding phase are entered into the DSA 100 software and along with the captured image of the droplet, the IFT can be calculated using the Pendant prop technique. With respect to the contact angle, saturated core plugs are placed in glass containers filled with the chosen fluid (e.g., a brine sample or a fracturing fluid sample). A drop of a hydrocarbon sample (e.g., mineral oil, crude from the formation, etc.) is placed onto the substrate selected to represent the in-situ condition. Once the drop became stable, an image of the droplet contact angle is captured by the DSA 100 and the contact angle can be measured. The contact angle can be measured using the Young-Laplace method.

In one embodiment, some of the fracturing fluids are selected for further tests depending on their performance in the wettability tests, e.g., fluids that would cause a shift in the contact angle of the rock samples from oil-wet conditions (contact angle greater than 90 degrees) to water-wet condition (contact angle less than 90 degrees).

Figure 5:
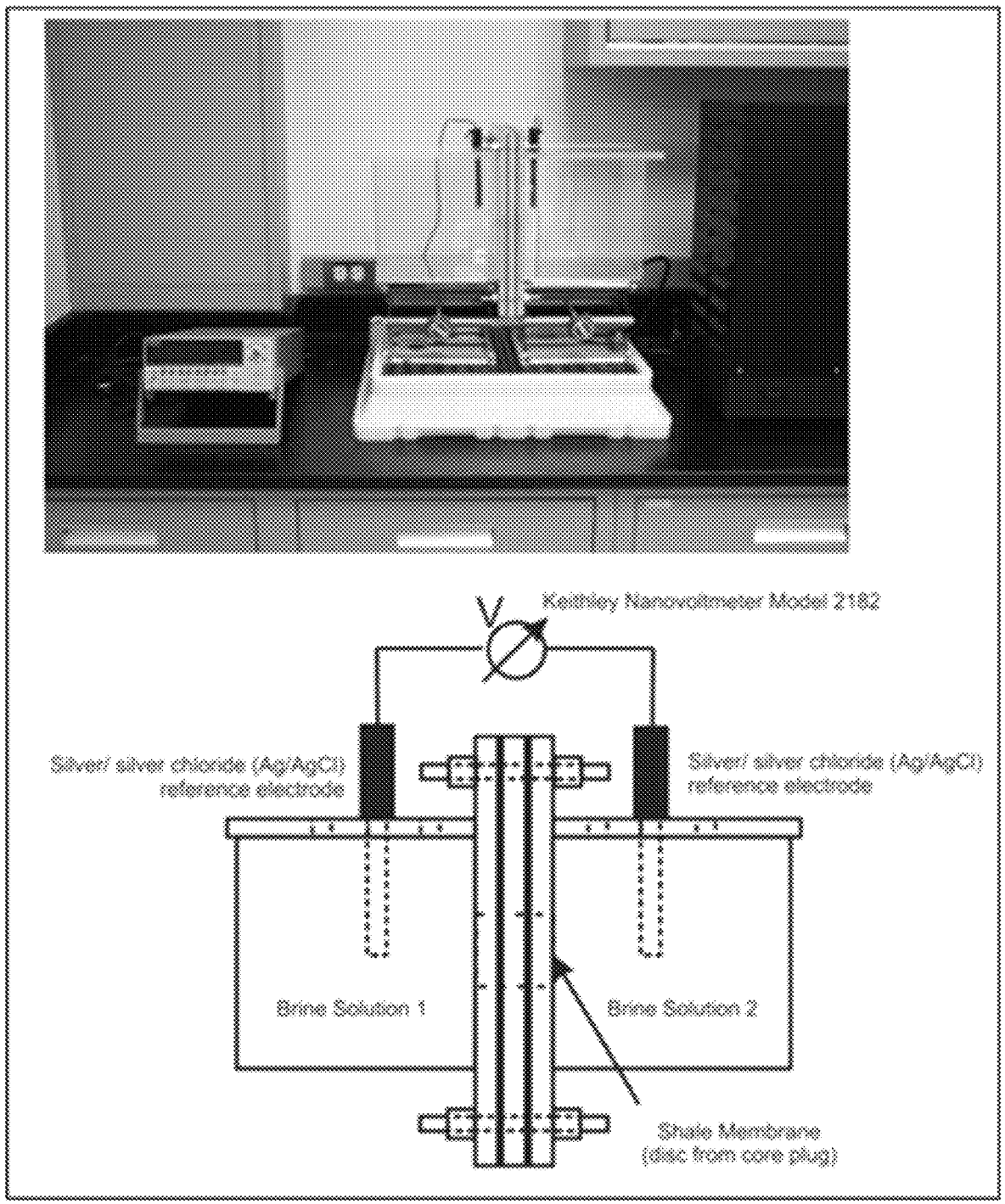
FIG. 5 illustrates electrochemical potential apparatus setup, according to one embodiment.

Conducting Ion Selectivity Test: In one embodiment, the ion selectivity of the various fracturing fluids is evaluated. The ion selectivity test measures the voltage drop across a rock sample that is in contact with fracturing fluids of different salinities. The ion selectivity reflects the ability of the rock to restrict anions from passing through. Methods for measuring ion selectivity are known in the art, e.g., as disclosed in "A Rapid, Rigsite Deployable, Electrochemical Test for Evaluating the Membrane Potential of Shales" by Al-Bazali et al., 2005, SPE Annual Technical Conference and Exhibition, 9-12 Oct. 2005, incorporated herein by reference in its entirety. The electrochemical potential (ECP) data is used to calculate ion selectivity following published works. Correlation is made with other rock property data including, but not limited to: porosity, permeability, cation exchange capacity (CEC), mineralogy and pore size distribution (FIG. 5).

NMR Test Procedures and Data Processing: The NMR measurements may be performed with a Tecmag, Apollo LF1 spectrometer at a Larmor frequency of approximately 2 MHz with a 41-mm probe capable of measuring echo spacing to 200 microseconds. The spectrometer can accommodate cylindrical samples up to about 5 cm in length and up to about 4 cm in diameter, having a minimum sample pore volume of 0.2 cm³. NMR system frequency, RF coil, and pulse widths are tuned daily. The NMR system response (fluid volume versus amplitude) is verified daily using known standards.

The core samples are allowed to equilibrate at system temperature prior to the NMR measurements. The transverse relaxation times (T2) and longitudinal relaxation times (T1) are determined simultaneously using a two-dimensional pulse sequence (T1CVX) with a minimum inter-echo spacing of 200 microseconds. T1CVX pulse sequence is repeated a sufficient number of times to achieve a reasonably good signal to noise ratio. All NMR measurements may be conducted at 30° C.

For the collected data from each sample, the echo trains are analyzed through a regularized multi-exponential process using Matlog. This process fits the data and divided the data into relaxation time increments. The amplitude value for each increment is calculated. The amplitude values are converted to porosity using calibration values and the sample bulk volume.

The T1/T2 ratio provides a robust methodology to identify and quantify the different constituents occupying the pore space of organic-rich unconventional mudstone (shale). In such tight low permeability lithology containing liquid hydrocarbon, three main constituents can be identified based on the T1/T2 relationship including: (1) the volume percent of water tightly bound to clay minerals and possibly fully occupying nm to sub-nm diameter pores and capillaries, plus bitumen (CBWB); (2) relatively light oil in oil wet pore systems (OWP); and (3) the volume of oil and water in water wet porosity (WWP). The default T1/T2 cut-off values used for differentiating these component are based on existing publications and can be adjusted based on sample location and depth or on other relevant data and information.

Obtaining Disjoining Pressure (DP) Measurements: "Disjoining pressure" refers to the pressure difference between a fluid in the pore space of a rock sample and that in a bulk solution at the same depth. In one embodiment, disjoining pressure measurements are obtained to quantify the interaction between hydrocarbons and the rock surfaces—as separated by the fracturing fluids as the electrolytes.

Methods to measure disjoining pressure are known in the art, e.g., as disclosed in "Measurement of Critical Disjoining Pressure for Dewetting of Solid Surfaces" by Basu et al., Journal of Colloid and Interface Science, 181, 443-455 (1996), incorporated herein by reference in its entirety.

Obtaining Cation Exchange Capacity (CEC) Measurements: "Cation exchange capacity" (CEC) is the capacity of a material, such as clay or soil, for ion exchange of positively charged ions between the material and the surrounding fluid (water), or the quantity of positively charged ions (cations) that the material can accommodate on its negatively charged surface. The crystal structure of rock in a formation allows it to swell in the presence of an aqueous fluid, e.g., the fracturing fluid. The swell may lead to a change in the rheological properties and/or the rate of penetration.

In one embodiment, certain select fracturing fluids are tested with a plurality of rock samples to determine their impact on the swelling properties of the rock samples, e.g., the CEC expressed as million equivalent per 100 g, or more commonly as milli-equivalent (meq) per 100 g. CEC can also be expressed in terms of its contribution per unit pore $Q_v$. Techniques to measure CEC are known in the art, e.g., wet chemistry such as conductometric titration, multiple salinity and membrane potential. Conductometric titration tests may include any of methylene blue method, ammonium acetate method, benzyl ammonium chloride method, malachite green method, or silver-thiourea method.

CEC tests can be carried out with a number of fracturing fluids and with a number of representative rock samples for various time periods, e.g., from several minutes to several days or weeks, depending at least in part, the diffusion of the fluid into the samples. In one embodiment, the CEC tests are carried out under different conditions of pressure and temperature representing the conditions of the formation, as the final swelling volume depends at least in part on the temperature and pressure of the rock samples.

In one embodiment, in addition to or instead of a CEC test, a linear swell meter (LSM) test is employed to determine and/or represent the swelling characteristics of a rock sample in the presence of the various tested fracturing fluids. Swelling characteristic methods include those described in "Shale/Mud Inhibition Defined with Rig-Site Methods" SPE Drilling Engineering, Chenevert et al. (September 1989) incorporated herein by reference.

Conducting Adsorption/Desorption Simulation Tests: In one embodiment to simulate the stimulation process, the adsorption/desorption of various fracturing fluid samples are evaluated over certain defined length of time and under various conditions to evaluate cation exchange and charge compensation behaviors in an adsorption/desorption simulation test. The test is carried out on a plurality of rock samples, brine samples, and fracturing fluid samples to investigate the impact of different cations exchanged in the structure of clay minerals or adsorbed to the surface of rock-forming minerals on wettability and related oil production from hydrocarbon bearing rocks.

In the test, the cation exchange processes are coupled with the variation in the hydrated radius of the ions and depend on the electrostatic attraction of the water molecules to the ions. The charges of the ions dictate the radius of the hydrated ions and the thickness of the water layer on the surface of the mineral. The forces coupled with the layer thickness drive the adsorption of hydrocarbons to the rock surface and related production. The test is to evaluate the changes in the rock properties as to the capacity to adsorb/desorb organic molecules of fracturing fluids for a given rock formation, and providing kinetic measurements of rock-fluid interaction.

The adsorption/desorption simulation test is carried out with rock samples classified according to the International Union of Pure and Applied Chemists (IUPAC), where equivalent pore diameter widths <2 nm are termed micropores, 2-50 nm are mesopores, and those >50 nm are referred to as macropores. While not being bound to theory, it is believed that water present in shale formations occupies micropore and smaller mesopores by mechanical capillary condensation forces. Owing to their polarity, water molecules are bound to clay minerals and their associated exchange cations by electrostatic hydration and Van der Waals forces.

The adsorption/desorption simulation tests can be carried out with rock samples of different sizes and geometries, e.g., core plugs in the form of discs, smaller samples in the form of powder or grains. The tests can be carried out in batch mode, or in a continuous mode with a packed bed of rock samples. In the batch mode, the dynamic response of solid-fluid system can be measured after a step change of conditions, e.g., mixing the solid materials with a fracturing fluid with known initial concentration and measuring the composition changes of the fluid as a function of time. In the continuous flow mode with solid materials packed in a column with the tested fluid flowing continuously through the column, kinetic data is obtained by monitoring the effluent's response to a change of inlet fluid, e.g., a concentration step change at the inlet and monitoring concentration profile at the outlet of the column as a function of time.

In one embodiment, the adsorption/desorption simulation test is carried out with reservoir rock samples collected from preserved core or core that still contains significant crude oil saturation. If a core with natural oil saturation is not available, plugs from the targeted reservoirs will be first cleaned and then saturated with crude oil for a period of time, e.g., from a few hours, a few days, a few weeks, etc. In some embodiments, the tests are carried out with rock samples that are saturated with model hydrocarbons representative of certain crude oil classes (aliphatic, aromatic, resins, asphaltenes), to evaluate the adsorption/desorption processes as a result of cation exchange processes and related changes in wettability In one embodiment of the test, the rock samples undergo a standard of cation exchange process, wherein the samples undergo a variety of cation exchange treatment, e.g., with each test employing with a different brine comprising multivalent/monovalent cations (such as $Mg^{2+}$, $Ca^{2+}$, $Na^+$ and $K^+$) and mixtures thereof, at different concentrations and different saturation time, to evaluate the cation exchange and charge compensation behavior and its impact on the hydrocarbon recovery of the brine(s) for use in the fracturing fluid. In another embodiment, the samples undergo a variety of cation exchange treatment with fracturing fluids with additives. The samples are soaked in the fracturing fluid for a period of time, e.g., from hours to days, in either batch mode or continuous mode.

The soak time in the test for each experiment with a brine/fracturing fluid can vary from a few hours to a few days, a few weeks, or a few months, simulating the shut-in time for shale reservoirs. Other variations in experimental parameters include but are not limited to fracturing fluid chemistry (e.g., brine compositions in terms of cation species and concentration, additive types and concentration), pH of the brine/fracturing fluid, pressure, temperature, and times.

In one embodiment of a batch test, the samples are filtered with the liquid being analyzed over time to monitor compositional changes, with the mass transfer rate inside the core samples being calculated based on the compositional changes of the liquid samples over time. In another embodiment of a continuous test, the rock particles are packed inside a column with fracturing fluid continuously flowing down the packed bed at controlled rates. The fracturing fluid composition and flow is controlled to provide a step change of the inlet composition that will propagate through the packed bed. The fluid composition exiting the bottom of the packed bed is measured as a function of time. Kinetic data is obtained by analyzing the concentration profile over time at the outlet as a response to the change in the concentration at the inlet.

In one embodiment after the brine is removed from a rock sample (e.g., using a centrifuge), the sample is transferred to a dialysis system for electrical conductivity measurements. In another embodiment of the test, the samples are observed and pictures are taken, along with various measurements obtained over a period of the time, including but not limited to porosity/pore volume/permeability of the rock samples before and after the test, amount of oil released over a period of time (e.g., sample change in weight of the sample after and before saturation with brine/fracturing fluid), contact angle tests after exposure to the fracturing fluid, oil spreading potential, etc. The samples can also be processed using micro/nano computed tomography (CT) to characterize the minerals reacting to injection brine. X-ray CT scanning of slices across the plan of the saturated samples can be taken to aid the visualization of fluid imbibition into the rock matrix, to help with the selection/identification of the optimal fracturing fluid for a certain rock type.

In one embodiment, the test is carried out for the same rock sample with different fracturing fluid samples (in series) for different periods of time, simulating different shut-in periods. This type of test can be useful for use in simulating fracturing operations and/or finding solutions with operational issues, e.g., correcting the damages caused by a particular fracturing fluid with the use of a different fracturing fluid.

From the tests, the amount of oil, e.g., recovery efficiency, of the different fracturing fluids tested can be estimated based on the release/oil production as a function of time and/or properties of the rock samples. Based on the recovery efficiency, a number of "best" or "optimal" fracturing fluids can be selected for other tests such as a free imbibition test, or for wettability measurements.

"Forced" Imbibition Test: In one embodiment after the adsorption/desorption simulation tests and optionally after wettability measurements, imbibition measurements are carried out with certain brines/fracturing fluids to quantify hydrocarbon release due to fracturing fluid-oil-rock interactions under a variety of conditions, e.g., pressure and temperature, to simulate field performance with high pressure injection ("forced imbibition"). The fluids can be selected for the imbibition test based on acceptable performance from other tests and measurements, e.g., desirable wettability characteristics and/or oil recovery rates from the adsorption/desorption simulation test.

The tests can be carried out under various conditions, e.g., low-pressure tests for standard imbibition; high-pressure tests for counter-current imbibition; and scale up to field performance simulation. Examples of dynamic imbibition tests include tests at low pressure (e.g., <1,000 psi) and high pressure (e.g., 3,000 to 5,000 psi), providing measurements as how fast the imbibition process takes place in the pore scale. The tests can be carried out with a variety of core samples to simulate field performance using different selected fracturing fluids.

In the imbibition tests, cylindrical core samples can be used. The samples can be of varying lengths (e.g., from 2 to 24 cm) and diameters (e.g., 1 to 5 cm). In one embodiment of the test, multiple samples (from the same or different rock formations) are first saturated with different hydrocarbon samples, including model hydrocarbons (e.g., mineral oils), then tested with the same or different fracturing fluids for the wetting phase. In another embodiment, the core samples are tested as is. Some of the cores can be epoxy sealed at one end, some cores are epoxy sealed to leave only one end open to imbibition, some cores can be sealed such that only the lateral surface is open, some cores are sealed such that only the ends are open to imbibition. Some of the cores can be split or cut partially or entirely lengthwise, with a different rock being inserted to simulate a dominating fracture.

The tests are carried out under pressure, e.g., mounted into a metal core holder ("imbibition cell") with applied pressure (e.g., $N_2$ of at least 500 psi, and up to 4000 psi) and heat, simulating the pumping of fracturing fluid under pressure. The samples are kept under pressure for varying periods of time to simulate shut-in periods. Selected fracturing fluid is injected into one inlet of the cell, with the effluent (i.e., oil and fracturing fluid) being collected from the outlet of the cell. Oil production over time is mainly produced by water imbibition from the fracture into the matrix, with the fracture providing a path for expelled oil to flow to the outlet.

Figure 6:
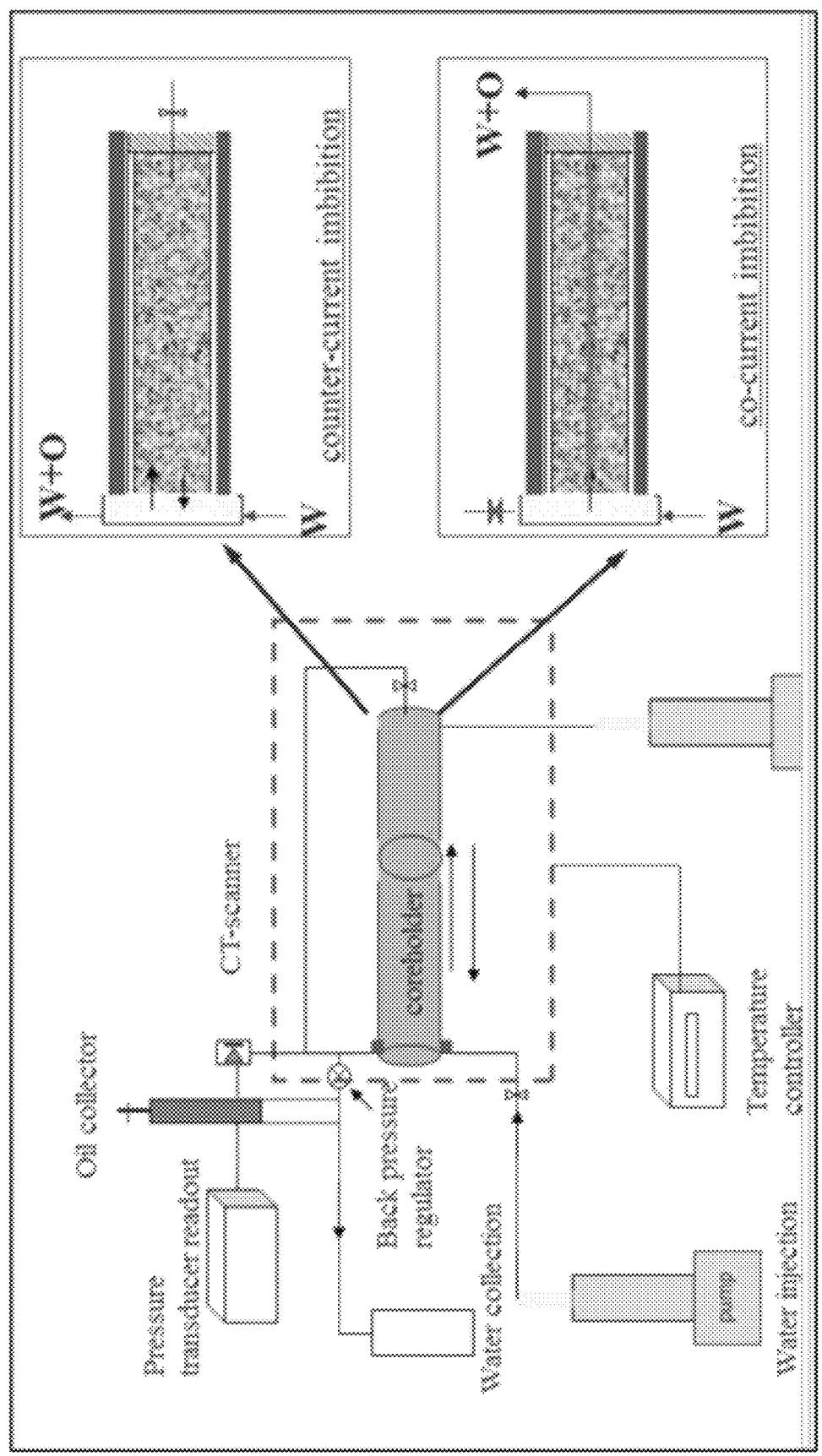
FIG. 6 illustrates a schematic diagram of an imbibition test setup, according to one embodiment.

The imbibition tests can be carried out at a constant pressure in one embodiment, and with step by step increase in pressure in another embodiment to evaluate the effect of injection pressure on the imbibition potential. At the end of the test, tracer tests can be conducted to validate how much water is imbibed into the core by comparing before the water imbibition test. Oil recovery rate can be measured and correlated as a function of various factors, including but not limited to imbibition time, open surface area, core length (in terms of the geometry of the core sample), fracturing fluid concentration, composition, oil properties (e.g., viscosity), viscosity ratio of oil vs. fracturing fluid. FIG. 6 illustrates a schematic diagram of an imbibition test setup, according to one embodiment.

Modeling Optimizing Fracturing Fluid Design & Selection: Models for predicting the recovery of hydrocarbons, selection of fracturing fluid(s) for formation(s) with certain rock characteristics can be developed as related to predicted performance, characteristics, predicted properties with respect to wettability, swelling characteristics, etc.

can be developed from the input data collected in the library. New test results from both laboratory and field tests can be added to the library over time. Larger sample size (e.g., fracturing fluids, types of rock formation, number of field tests, number of experiments, etc.) leads to increased precision for the models. Linear and/or non-linear regression analyses can be used to develop models; with various forms of functions developed including power function, an exponential function, a polynomial function, a linear function, and combinations; and optimization techniques known in the art including but not limited to sort-and-rank of analogies, multi-variable minimization, and empirical proxies from experimental design method.

The models can take into account various parameters as input data, including:

a first parameter characterizing the petrophysical/geochemistry properties of the reservoir rocks (e.g., permeability, surface area, pore volume, porosity, matrix density), a second parameter characterizing the properties of the hydrocarbons (e.g., polarity, acidity and molecular contents), a third parameter characterizing the properties of the formation brine (e.g., composition and concentration of monovalent and/or multivalent cations), an optional fourth parameter characterizing the properties of the fracturing fluids if additives are added (e.g., concentration and composition of the additives), an optional fifth parameter with rock-fluid interactions from the various tests (e.g., CEC, wettability, ion selectivity, contact angle, disjoining pressure), an optional sixth parameter characterizing the fractures inherent in the rock (e.g., micro/nano-CT imaging), and a seventh parameter correlating the mass transfer and kinetic measurements from the adsorption/desorption simulation and/or imbibition tests (e.g., diffusivity, flow rate, oil recovery/production, oil recovery % as a function of time). The seventh parameter with mass transfer and imbibition functions can be obtained from history match of imbibition recovery curve(s) from the experiments.

Depending on the desired complexity and available computing resources, the models can be relative (e.g., providing a relative ranking between various fracturing fluids (in terms of composition/concentration of brines/additives), or they can be absolute (e.g., making quantitative estimates with or without calibration to the external data in terms of predicting oil recovery). The simulations can be performed at different hydraulic fracturing conditions, e.g., pressure, shut-in time, etc., thus allowing optimizing the hydraulic fracturing procedure.

A plurality of models may be derived for different rock formation types (e.g., different mineral classifications), different brines (e.g., having different types of salts and/or combinations of salts), fracturing fluids (e.g., having different additives and/or combinations of additives). In some embodiments, the models can evaluate the effects of different salt ions (e.g., Na+, K+, Mg+, etc.) on the adsorption/desorption characteristics of the rock samples.

From the models, optimal fracturing fluids can be selected or designed for a particular rock type or reservoir. The developed models can also be used to generate predicted values with respect to performance of fracturing fluids in certain rock formations. The predicted values may be statistically compared with measured values from pilot trials and/or field trials to provide one or more statistical measurements as to the accuracy of the models or to fine tune the models. The model parameters can be optimized to scale up the imbibition test from the core scale to pilot scale, and to field tests, with the models being used to forecast the water imbibition potential.

In one embodiment, mechanistic modeling methods are used to enhance the statistical methods in addressing key physical mechanisms potentially impacting the recovery process as observed at various scale levels, from laboratory tests to field-scale performance results. The modeling efforts include numerical simulation to history match or replication of the lab-scale behavior before scaling up to field-scale performance prediction. This provides key understanding of influencing physics and chemistry involved in the imbibition process for optimizing the design of fracturing fluids and executing field applications for each shale play or tight rock formation.

In one embodiment, the developed models are used to select and/or for the design of a fracturing fluid or fluids to be used for a particular formation, e.g., a newly explored or newly investigated formation. In another embodiment, the models can be used to help resolve an operational issue with an existing, with data from the library being used to predict and/or correct an operational issue with the selection, design, changing the composition the fluids to be injected for each of the hydraulic fracturing stages. In yet another embodiment, the results from a comprehensive test library together with the models, lead to the tailoring/optimization of fracturing fluid(s) for the shale/tight formation under consideration. This approach significantly saves time & resources compared to the trial-and-error approaches in the prior art.

EXAMPLES

The following examples are intended to be non-limiting.

Example 1. In this screening experiment, a number of wettability tests with various fracturing fluids are carried out with a plurality of rock samples. Contact angle and/or surface tension (IFT) measurements are conducted with a Kruss DS100 apparatus, equipped with software to capture contact angle and IFT data. The contact angle can be measured using the Young Laplace method. The IFT measurement can be measured using Pendant drop techniques. Measurement data is collected for the library, correlating wettability characteristics of the fracturing fluid samples with the rock samples. A number of fracturing fluid candidates can be selected for further experiments, CEC and/or the adsorption/test.

Example 2. Based on the screen test results in Example 1, e.g., wettability tests with fracturing fluids giving the best responses for rock samples, a few fracturing fluid candidates are selected for the adsorption/desorption test. Each rock sample, e.g., a core disk, is first saturated with a select hydrocarbon sample for 24 hours. The sample is then centrifuged for a few minutes and decanted. The rock sample is then saturated with a selected fracturing fluid at reservoir temperature. The release of oil film from the rock surface can be observed and recorded. Oil production by water imbibition can also be monitored and recorded. The produced oil can be qualitatively estimated at the end of the test.

Example 3. After the adsorption/desorption test, the rock samples in Example 2 are tested to measure the contact angle and spreading potential to confirm and/or select the fracturing fluids giving a combination of desirable oil production as well as wettability characteristics.

Example 4. From the wettability measurements, certain fracturing fluids are selected for the imbibition tests simulating hydraulic fracturing conditions. The test system includes a high pressure and temperature coreholder, allowing tests to run at elevated temperatures up to 400° F. and pressures up to 3000 psi, and for both counter-current and co-current free imbibition, and co-current forced imbibition. This core holder can hold a core plug with lengths from 3 to 12 inches, and can be either vertically or horizontally positioned. For some tests, the coreholder is positioned vertically to study gravity effects. In addition, a high resolution CT-scanner (with a resolution of 50 microns) is used to monitor water imbibition from fracture into the matrix and observe its behavior in the matrix. CT-scanning is also used to study the fracture network and its effect on water imbibition behavior. FIG. 3 is a schematic diagram of an imbibition test setup.

In the counter-current imbibition test, the core is mounted in the coreholder with an applied pressure simulating the desired pressure for hydraulic fracturing, e.g., 1000 psi. The core holder is heated to reservoir temperature approximately 120° F., and fresh crude oil is injected to displace the residential oil and mobile water if present. The produced water is collected for water chemistry analysis. Approximately 10 PV of crude oil is injected to re-condition the core and re-establish the initial water saturation. The core is then subjected to counter-current free imbibition. The fracturing fluid under evaluation is run through the open end face of the core with the other end closed. The fluid flows through the end face and both oil and collected downstream of the cycle loop. The produced oil is measured versus time. When oil production ceases, the test is switched into forced imbibition by closing the downstream valve and opening the other end of the core. The forced fluid injected through the core. The forced imbibition continued until no oil production is observed.

In the co-current imbibition test, a core sample with oil saturation is cut into two halves and a high permeability sandstone wafer with a thickness of ~0.125 inch is sandwiched to make a new core having a fracture in the middle. This core configuration provides increased surface areas for testing. The fracturing fluid under evaluation is injected through the core fracture and oil and water is produced from the other end of the core. No forced imbibition was conducted after free imbibition due to this fracture.

The core can be CT-scanned at the end of imbibition test to obtain the residual saturation distribution (or remaining oil saturation).

Example 5. Both statistical method and mechanistic method are being used to analyze the test results obtained from various laboratory measurements. Statistical method correlates multiple test measurements and results to observe key parameters that affect the potential outcomes for prediction. These include, but not limited to, rock type and characteristics, fluid type and compositions, and test conditions or constraints (temperature, pressure, etc.). Mechanistic modeling uses numerical methods to simulate rock-fluid interaction and flow behavior. Various models of different scales are used to replicate lab-scale results observed prior to predicting field-scale performance. These numerical mechanistic models provide the understanding of the underlying physics that affect the observed outcomes from the lab measurements and from the statistical method. A combination of the two approaches, statistical and mechanistic, supports the prediction forecasting.

Those of ordinary skill in the art will appreciate that various modifications may be made to the embodiments disclosed herein. For example, one embodiment of a method for optimizing fracturing fluid compositions for injection into a subterranean formation includes providing a plurality of rock samples being representative of a rock matrix within a subterranean formation containing hydrocarbons for recovery; providing a plurality of brine samples being representative of formation brines of the subterranean formation; providing a plurality of hydrocarbon samples being representative of hydrocarbons recoverable from the subterranean formation; characterizing the rock samples to obtain one or more rock parameters representing geochemistry properties of the rock samples, petrophysical properties of the rock samples, or any combination thereof; characterizing the brine samples to obtain one or more brine parameters representing alkalinity properties of the brine samples, salinity properties of the brine samples, total dissolved solids (TDS) properties of the brine samples, or any combination thereof; characterizing the hydrocarbon samples to obtain one or more hydrocarbon parameters representing acidity properties of the hydrocarbon samples, polarity properties of the hydrocarbon samples, molecular characteristics properties of the hydrocarbon samples, or any combination thereof; synthesizing at least two fracturing fluid samples based on the rock parameters, the brine parameters, the hydrocarbon parameters, or any combination thereof; and conducting a test on at least one rock sample and the at least two fracturing fluid samples to evaluate rock-fluid interactions. The test comprises an interfacial tension test to determine contact angle, zeta potential, wettability, interfacial tension properties, or any combination thereof; an ion selectivity test to determine ion selectivity properties; a cation exchange capacity test to determine cation exchange capacity properties; a disjoining pressure test to determine disjoining pressure properties; an adsorption desorption simulation test to determine cation exchange and charge compensation properties; a forced imbibition test to evaluate kinetic and mass transfer properties; or any combination thereof. The method further includes preparing at least one fracturing fluid for injection into the subterranean formation based on at least two criteria, wherein the criteria comprises the rock parameters, the brine parameters, the hydrocarbon parameters, the contact angle properties, the zeta potential properties, the wettability properties, the interfacial tension properties, the ion selectivity properties, the cation exchange capacity properties, the disjoining pressure properties, the cation exchange and charge compensation properties, the kinetic and mass transfer properties, or any combination thereof.

As an example, one of ordinary skill in the art may implement this method using the interfacial tension test only. Alternatively, one of ordinary skill in the art may implement this method using the cation exchange capacity test only. Alternatively, one of ordinary skill in the art may implement this method using a combination of the interfacial tension test and the disjoining pressure test only. Alternatively, one of ordinary skill in the art may implement this method using a combination of the interfacial tension test, the adsorption desorption simulation test, and the forced imbibition test only. Various other alternatives are also possible.

As an example, one of ordinary skill in the art may implement this method using a combination of the rock parameters criteria and the brine parameters criteria only. Alternatively, one of ordinary skill in the art may implement this method using a combination of the zeta potential properties criteria and the wettability properties criteria only. Alternatively, one of ordinary skill in the art may implement this method using a combination of the wettability properties criteria, the interfacial tension properties criteria, and the disjoining pressure properties criteria only. Various other alternatives are also possible.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention, inclusive of the stated value and has the meaning including the degree of error associated with measurement of the particular quantity. This term "about" generally refers to a range of numbers that one of ordinary skill in the art would consider as a reasonable amount of deviation to the recited numeric values (i.e., having the equivalent function or result). For example, this term "about" can be construed as including a deviation of ±10 percent of the given numeric value provided such a deviation does not alter the end function or result of the value. Therefore, a value of about 1% can be construed to be a range from 0.9% to 1.1%.

As used in this specification and the following claims, the terms "comprise" (as well as forms, derivatives, or variations thereof, such as "comprising" and "comprises") and "include" (as well as forms, derivatives, or variations thereof, such as "including" and "includes") are inclusive (i.e., open-ended) and do not exclude additional elements or steps. For example, the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Accordingly, these terms are intended to not only cover the recited element(s) or step(s), but may also include other elements or steps not expressly recited.

While various embodiments are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. Also, the terms in the claims have their plain, ordinary meaning unless otherwise explicitly and clearly defined by the patentee. If there is any conflict in the usages of a word or term in this specification and one or more patent or other documents that may be incorporated herein by reference, the definitions that are consistent with this specification should be adopted.

Furthermore, as used herein, the use of the terms "a" or "an" when used in conjunction with an element may mean "one," but it is also consistent with the meaning of "one or more," "at least one," and "one or more than one." Thus, it is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. As used herein, the use of "may" or "may be" indicates that a modified term is appropriate, capable, or suitable for an indicated capacity, function, or usage, while taking into account that in some circumstances the modified term may sometimes not be appropriate, capable, or suitable. Furthermore, unless explicitly dictated by the language, the term "and" may be interpreted as "or" in some instances.

It is understood that when combinations, subsets, groups, etc. of elements are disclosed (e.g., combinations of components in an item, or combinations of steps in a method), that while specific reference of each of the various individual and collective combinations and permutations of these elements may not be explicitly disclosed, each is specifically contemplated and described herein. By way of example, if an item is described herein as including a component of type A, a component of type B, a component of type C, or any combination thereof, it is understood that this phrase describes all of the various individual and collective combinations and permutations of these components. For example, in some embodiments, the item described by this phrase could include only a component of type A. In some embodiments, the item described by this phrase could include only a component of type B. In some embodiments, the item described by this phrase could include only a component of type C. In some embodiments, the item described by this phrase could include a component of type A and a component of type B. In some embodiments, the item described by this phrase could include a component of type A and a component of type C. In some embodiments, the item described by this phrase could include a component of type B and a component of type C. In some embodiments, the item described by this phrase could include a component of type A, a component of type B, and a component of type C. In some embodiments, the item described by this phrase could include two or more components of type A (e.g., A1 and A2). In some embodiments, the item described by this phrase could include two or more components of type B (e.g., B1 and B2). In some embodiments, the item described by this phrase could include two or more components of type C (e.g., C1 and C2). In some embodiments, the item described by this phrase could include two or more of a first component (e.g., two or more components of type A (A1 and A2)), optionally one or more of a second component (e.g., optionally one or more components of type B), and optionally one or more of a third component (e.g., optionally one or more components of type C). In some embodiments, the item described by this phrase could include two or more of a first component (e.g., two or more components of type B (B1 and B2)), optionally one or more of a second component (e.g., optionally one or more components of type A), and optionally one or more of a third component (e.g., optionally one or more components of type C). In some embodiments, the item described by this phrase could include two or more of a first component (e.g., two or more components of type C (C1 and C2)), optionally one or more of a second component (e.g., optionally one or more components of type A), and optionally one or more of a third component (e.g., optionally one or more components of type B).

Unless defined otherwise, all technical and scientific terms used herein have the same meanings as commonly understood by one of skill in the art to which the disclosed invention belongs.

This written description uses examples to disclose the invention, including the best mode, and also to enable any person skilled in the art to make and use the invention. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All citations referred herein are expressly incorporated by reference.

The invention claimed is:

1. A method for injecting a fracturing fluid composition into a subterranean formation, the method comprising:
    preparing a fracturing fluid composition for injection into a subterranean formation, wherein the fracture fluid composition is selected based on rock-fluid interactions that are determined from:
        an interfacial tension test to determine contact angle properties, zeta potential properties, wettability properties, interfacial tension properties, or any combination thereof;
        an ion selectivity test to determine ion selectivity properties;
        a cation exchange capacity test to determine cation exchange capacity properties;
        a disjoining pressure test to determine disjoining pressure properties;
        an adsorption desorption simulation test to determine cation exchange and charge compensation properties;
        a forced imbibition test to evaluate kinetic and mass transfer properties; or
        any combination thereof; and
    injecting the fracturing fluid composition into the subterranean formation to increase production of hydrocarbons from the subterranean formation.

2. The method of claim 1, further comprising:
    providing a plurality of rock samples being representative of a rock matrix within the subterranean formation;
    providing a plurality of brine samples being representative of formation brines of the subterranean formation;
    providing a plurality of hydrocarbon samples being representative of hydrocarbons recoverable from the subterranean formation;
    characterizing the rock samples to obtain one or more rock parameters representing geochemistry properties of the rock samples, petrophysical properties of the rock samples, or any combination thereof;
    characterizing the brine samples to obtain one or more brine parameters representing alkalinity properties of the brine samples, salinity properties of the brine samples, total dissolved solids (TDS) properties of the brine samples, or any combination thereof; and
    characterizing the hydrocarbon samples to obtain one or more hydrocarbon parameters representing acidity properties of the hydrocarbon samples, polarity properties of the hydrocarbon samples, molecular characteristics properties of the hydrocarbon samples, or any combination thereof.

3. The method of claim 2, further comprising:
    compiling a database comprising the rock parameters, the brine parameters, the hydrocarbon parameters, the contact angle properties, the zeta potential properties, the wettability properties, the interfacial tension properties, the ion selectivity properties, the cation exchange capacity properties, the disjoining pressure properties, the cation exchange and charge compensation properties, the kinetic and mass transfer properties, or any combination thereof;
    generating at least one model representative of the subterranean formation utilizing information from the database; and
    performing mechanistic modeling using numerical simulation or experimental design methods to estimate hydrocarbon recovery from the subterranean formation for the fracturing fluid composition being injected into the subterranean formation.

4. The method of claim 3, further comprising:
    adding to the database hydrocarbon recovery data obtained from injection of the fracturing fluid composition into the subterranean formation; and
    updating the model representative of the subterranean formation based on the hydrocarbon recovery data; and
    updating the estimate of hydrocarbon recovery from the subterranean modeling methods.

5. The method of claim 4, wherein updating the estimate of hydrocarbon recovery further comprises performing mechanistic modeling, statistical modeling, or any combination thereof with the updated model.

6. The method of claim 3, wherein the model is used to identify fracturing fluid compositions having an estimated hydrocarbon recovery from the subterranean formation hydrocarbon above a predetermined threshold.

7. The method of claim 2, further comprising:
    compiling a model correlating (a) the ion selectivity properties, the cation exchange capacity properties, the disjoining pressure properties, or any combination thereof with (b) the rock parameters, the brine parameters, the hydrocarbon parameters, the contact angle properties, the zeta potential properties, the wettability properties, the interfacial tension properties, the cation exchange and charge compensation properties, the kinetic and mass transfer properties, or any combination thereof.

8. The method of claim 2, further comprising:
    compiling a model correlating (a) the contact angle properties, the zeta potential properties, the wettability properties, the interfacial tension properties, or any combination thereof with (b) the rock parameters, the brine parameters, the hydrocarbon parameters, the ion selectivity properties, the cation exchange capacity properties, the disjoining pressure properties, the cation exchange and charge compensation properties, the kinetic and mass transfer properties, or any combination thereof.

9. The method of claim 2, further comprising:
    characterizing fractures in the rock samples by micro-CT imaging, nano-CT imaging, or both; and compiling a model correlating (a) the fractures in the rock samples with (b) the rock parameters, the brine parameters, the hydrocarbon parameters, the contact angle properties, the zeta potential properties, the wettability properties, the interfacial tension properties, the ion selectivity properties, the cation exchange capacity properties, the disjoining pressure properties, the cation exchange and charge compensation properties, the kinetic and mass transfer properties, or any combination thereof.

10. The method of claim 2, wherein the fracturing fluid composition for injection into the subterranean formation is synthesized based on the rock parameters, the brine parameters, the hydrocarbon parameters, or any combination thereof.

11. The method of claim 2, wherein the rock parameters comprise permeability, surface area, pore volume, porosity, matrix density, structural and crystal chemical variety, or any combination thereof.

12. The method of claim 1, wherein one or more of the interfacial tension test, ion selectivity test, cation exchange capacity test, disjoining pressure test, adsorption desorption simulation test, and forced imbibition test used to determine the rock-fluid interactions are conducted on at least one rock sample representative of a rock matrix within the subterranean formation and at least two fracturing fluid samples.

13. The method of claim 12, further comprising:
saturating the at least one rock sample with at least one hydrocarbon sample prior to conducting the forced imbibition test.

14. The method of claim 12, wherein:
at least one fracturing fluid sample is selected for the forced imbibition test based on the contact angle properties, the zeta potential properties, the wettability properties, the interfacial tension properties, or any combination thereof.

15. The method of claim 12, wherein:
each fracturing fluid sample has a different brine composition comprising varying concentrations of multivalent cations, monovalent cations, or any combination thereof;
the rock sample is saturated in each fracturing fluid sample for different periods of time;
and a hydrocarbon recovery rate is monitored over time to evaluate the cation exchange and charge compensation properties for each of the fracturing fluid samples.

16. The method of claim 1, wherein the fracturing fluid composition is injected into the subterranean formation in a hydraulic fracturing operation.

17. The method of claim 1, wherein the forced imbibition test comprises at least one of a counter-current imbibition test under pressure of at least 500 psi, a co-current imbibition test under pressure of at least 500 psi, or any combination thereof.

18. The method of claim 1, wherein the fracturing fluid composition comprises a fluid loss control additive, a nucleophilic agent, a biocide, a friction reducer, a pH reducing agent, a surfactant, a polymer, or any combination thereof.

19. The method of claim 1, further comprising verifying compatibility of components in the fracturing fluid composition before injection into the subterranean formation.

20. The method of claim 1, further comprising verifying compatibility of the fracturing fluid composition with at least one other fluid that will also be injected into the subtraenan formation before injection of the fracturing fluid composition into the subterranean formation.

21. The method of claim 1, wherein the fracturing fluid composition includes a surfactant and the compatibility of the surfactant is verified with at least one other additive of the fracturing fluid composition before injection of the fracturing fluid composition into the subterranean formation.

22. The method of claim 1, wherein the fracturing fluid composition includes a surfactant and the compatibility of the surfactant is verified with a temperature condition of the subterranean formation, a salinity of a formation brine of the subterranean formation, hydrocarbons in the subterranean formation, or any combination thereof before injection of the fracturing fluid composition into the subterranean formation.

23. The method of claim 1, wherein the fracturing fluid composition is injected into the subterranean formation for re-fracturing stimulation of the subterranean formation.

24. The method of claim 1, wherein the subterranean formation is a tight rock formation.

25. The method of claim 1, wherein the subterranean formation is a shale formation.

26. A method for injecting a fracturing fluid composition into a subterranean formation, the method comprising:
preparing a fracturing fluid composition for injection into a subterranean formation, wherein the fracture fluid composition is selected based on rock-fluid interactions stored in a database, wherein the database was generated using:
rock parameters representative of a rock matrix within the subterranean formation;
brine parameters being representative of formation brines of the subterranean formation;
hydrocarbon parameters being representative of hydrocarbons recoverable from the subterranean formation;
contact angle properties, zeta potential properties, wettability properties, interfacial tension properties, or any combination thereof generated from an interfacial tension test;
ion selectivity properties generated from an ion selectivity test;
cation exchange capacity properties generated from a cation exchange capacity test;
disjoining pressure properties generated from a disjoining pressure test;
cation exchange and charge compensation properties generated from an adsorption desorption simulation test;
kinetic and mass transfer properties generated from a forced imbibition test; or
any combination thereof; and
injecting the fracturing fluid composition into the subterranean formation to increase production of hydrocarbons from the subterranean formation.

27. The method of claim 26, wherein the fracturing fluid composition is injected into the subterranean formation in a hydraulic fracturing operation.

28. The method of claim 26, wherein the fracturing fluid composition is injected into the subterranean formation for re-fracturing stimulation of the subterranean formation.

29. The method of claim 26, wherein the subterranean formation is a tight rock formation.

30. The method of claim 26, wherein the subterranean formation is a shale formation.

31. The method of claim 26, wherein the fracturing fluid composition comprises a fluid loss control additive, a nucleophilic agent, a biocide, a friction reducer, a pH reducing agent, a surfactant, a polymer, or any combination thereof.

* * * * *